United States Patent [19]

Widmer

[11] 4,436,818

[45] Mar. 13, 1984

[54] APPARATUS FOR CARRYING OUT AN ANAEROBIC FERMENTATION OF ORGANIC SOLID MATTER FOR THE PURPOSE OF EXTRACTING A COMBUSTIBLE GAS

[76] Inventor: Peter Widmer, Ruchweid 202, 8911 Oberlunkhofen, Switzerland

[21] Appl. No.: 359,671

[22] PCT Filed: Jul. 10, 1981

[86] PCT No.: PCT/CH81/00077
§ 371 Date: Mar. 10, 1982
§ 102(e) Date: Mar. 10, 1982

[87] PCT Pub. No.: WO82/00299
PCT Pub. Date: Feb. 4, 1982

[30] Foreign Application Priority Data

Jul. 11, 1980 [CH] Switzerland .................. 5316/80

[51] Int. Cl.³ ............................................. C12M 1/02
[52] U.S. Cl. ............................. 435/316; 210/DIG. 9; 220/85 B; 48/197 A
[58] Field of Search .............. 435/287, 316; 220/85 B; 210/DIG. 9; 48/197 A

[56] References Cited

U.S. PATENT DOCUMENTS

| | | | |
|---|---|---|---|
| 2,991,983 | 7/1961 | Logan . | |
| 3,981,803 | 9/1976 | Coulthard | 435/316 X |
| 4,036,699 | 7/1977 | Quigg | 435/316 X |
| 4,060,175 | 11/1977 | Rysgaard, Sr. | 220/85 B |
| 4,100,023 | 7/1978 | McDonald | 71/9 X |
| 4,274,838 | 6/1981 | Dole et al. | 435/316 X |

FOREIGN PATENT DOCUMENTS

2752271 6/1978 Fed. Rep. of Germany .
2475571 8/1981 France .............................. 435/287

*Primary Examiner*—Ferris H. Lander
*Attorney, Agent, or Firm*—James E. Nilles

[57] ABSTRACT

A plant for production of fuel gas by anaerobic fermentation of organic materials comprises a pit-like hemispherical fermentation chamber and a flexible and foldable cover which, when inflated, has the form of a complementary hemisphere and is in open communication with the fermentation chamber at the horizontal equatorial plane. Organic materials are introduced into the fermentation chamber to the level of said plane. The cover is weighted to be foldingly contracted when unpressurized and to be inflated to its hemispherical form by generated gas.

5 Claims, 2 Drawing Figures

APPARATUS FOR CARRYING OUT AN ANAEROBIC FERMENTATION OF ORGANIC SOLID MATTER FOR THE PURPOSE OF EXTRACTING A COMBUSTIBLE GAS

The present invention relates to an apparatus for carrying out the anaerobic fermentation of organic solids for the purpose of extracting a combustible gas.

The increasing scarcity of crude oil on the world market and the massive price increases for light heating oil that were connected therewith in the recent past, as well as the warnings of the petroleum organizations that an end to the price increases is not to be expected within a foreseeable time and that restrictions in the supply cannot be ruled out in the future, urgently necessitate, alongside incisive economy measures, the development of alternative energy sources.

An essential contribution to energy conservation can be afforded by installations that release a combustible gas, which in the main comprises about 65% $CH_4$ and 35% $CO_2$, by means of anaerobic fermentation of organic solids.

Installations for producing gas by anaerobic fermentation of organic solids have been generally known world-wide since 1920 under the designation BIOGAS plants and have since that time been exhaustively dealt with and described in numerous publications.

In contemplating the world-wide scarcity and the accompanying incessant cost increase in fluid fossil fuel that is in progress, the production of combustible gas through anaerobic fermentation, mainly of animal excrement, as a substitute for prevailing heating oil, is again given the greatest attention.

The reason that BIOGAS apparatus is being installed almost exclusively in agricultural or animal keeping areas lies in the fact that these produce a cost-free waste product in animal excrement, rich in decomposable organic dry substance, the removal of which is today often attended by substantial difficulties.

The industrial economic necessity for rationalizing the production of useful animals in the past twenty years, and the new stall construction methods connected therewith, with its full or partially slotted floors as well as fully mechanized droppings-space devices, have the consequence that the excrement from intensive keeping of useful animals is produced in large quantities in the most thick flowing form, free from foreign matter such as longbladed straw or hay. As a result, substantial droppings storage capacity is necessary for the animal keeping operation, since the excrement for fertilizer use can only be brought out onto the area under cultivation during the precultivation period. The anaerobically fermentable organic dry substance needed for operation of a BIOGAS plant is thus available year around in sufficient quantities in agricultural operations that keep useful animals.

Depending upon the animals owned or the available amount of organic dry substance, by building a BIOGAS installation useful animal keeping operations can easily become self-sufficient for heat energy and also for electrical energy with a generator driven by an Otto cycle gas engine.

As a desired side effect, the almost complete odorlessness of the precipitate coming out of the BIOGAS plant signifies that its fertilizer value has been slightly increased through the anaerobic treatment.

In common usage, BIOGAS plant basically designates only an installation which performs the anaerobic fermentation process for the purpose of extracting a combustible gas. In contrast to apparatus for anaerobic fermentation of waste water residues from community or industrial purification plants, in which fermentation serves as a cleaning step for the purification plant, in BIOGAS plants the anaerobic decomposition process or the fermentation of the organic dry mass is shortened to the time period needed for an optimum yield of combustible gas.

The process and structure technology employed in fermentation towers of community or industrial purification installations for anaerobic fermentation of waste water residues, which as a rule contain about 2-3% decomposable dry substance, has long been known and need not here be further dealt with.

These conventional anaerobic fermentation systems, because of holding times for the water residue of between 30-60 days in the fermentation chamber, have a relatively low turnover rate, which can be expressed as residue processing in kilograms of decomposed BSB or organic dry substance = $kg/oTS/d$ = days. The large scale tanks needed for the operation of these conventional fermentation systems, with their long holding times, are in themselves unthinkable as structures in animal keeping operations.

The fermentation chambers of community or industrial waste water purification plants are, as a rule, charged with dry substance loads of about 3%, in relation to the total fermentation chamber volume. The fermentation systems in these installations are already hydraulically and mechanically overloaded with a dry material content of over 4% in relation to the total volume of the fermentation chamber.

Depending upon the type of animal and the stabling arrangement, animal excrement obtained from intensive animal keeping contains between 6% and 14% of dry substance per liter.

A dilution with water is out of the question because the dry material content per liter of fluid is thereby certainly reduced, while at the same time, however, the total volume increases in accordance with the degree of dilution, which again would bring the need for a volumetric enlargement of the fermentation chamber.

The fermentation chamber of a BIOGAS installation must thus be arranged as to its process and mechanical technology in such a way that a dry material charge of a maximum of 14% relative to the total fermentation chamber volume can be put through and kept in motion.

In the past two years a number of BIOGAS installations for anaerobic fermentation of animal excrement have been built and put into operation in Europe and the United States that have been closely modeled in their construction and mechanical equipment upon the fermentation systems employed in community water purification technology. With fex exceptions these BIOGAS installations have shown themselves to be processing technology disappointments, since the installed pumps or agitators were not capable of keeping in motion or circulating a fermentation chamber content having even as little as 7-9% dry material content.

To make clear the difficulty, there will now be briefly described the presently conventional structural form and process technology employed for BIOGAS plants.

As a fermentation chamber there is put up, almost without exception, a high tank of concrete, steel or plastic with, as a rule, a flat bottom, which is provided with an external insulation to prevent loss of process heat. The process temperature, of +36° C. as a rule is maintained by a heat exchanger built into the fermentation chamber. Hot water serves as the heat carrier. The plants are constructed according to the displacement principle with liquid seal (siphon), that is, the amount of biomass that is daily introduced into the fermentation chamber displaces out of the fermentation chamber, through the liquid seal, a like quantity of fermented biomass.

The time during which the biomass is held in the fermentation chamber amounts to between 12 and 20 days, depending upon the installation concept and the desired degree of decomposition by anaerobic fermentation. The fermentation chambers are charged with fresh biomass by means of pumps, in the course of which the fermentation chamber contents are turned over by means of pushers. To prevent floating cover which could form on the surface of the liquid due to specific light materials such as undigested fodder remains or grain hulls, there is in most cases a mechanical floating cover agitator, in the form of a half submerged bell screw built centrally into the tank cover. In this manner the floating materials are supposed to be mixed into the biomass. The combustible gas that accumulates between the tank cover and the surface of the fluid is conducted into a wet or dry gas accumulator through a connecting duct.

Many of the BIOGAS plants built in the recent past have miscarried because of the configuration of the fermentation chamber. As already mentioned, the bottoms of most of the BIOGAS plant fermentation chambers were made flat and the circulation pump drew the sediment meagerly across the bottom, sidewardly out of the tank. In consequence, only the residues that were directly adjacent to the suction inlet of the pump were drawn along, and the remaining residue mass built up more and more and attached itself so that even after a short time the fermentation chamber volume was substantially diminished and gas production fell off markedly. Certain builders take the trouble to meet this problem by building into the fermentation chambers stirring mechanisms that move slightly above the bottom. It is true that these stirring mechanism arrangements effect some remedy, but at the same time, they set narrow limits for the fermentation chamber dimensions. As in the case of conventional fermentation systems of waste water purification plants, the bottom of a BIOGAS fermentation chamber should be formed as a cone with a minimum 45° taper. The circulation pump should if possible be so arranged that sediments accumulated in the cone are drawn centrally out of the cone and are returned to the level of the fluid surface in the tank.

The gas formation in the fermentation chamber of a BIOGAS plant, in the event of proper functioning and operation of the plant, is constant during 24 hours a day. As a rule, the gas is conducted to the consuming device during the day and the night production must be stored. For gas storage there are offered wet and dry gas storage vessels of an operating pressure of about 200 mm. water column pressure. Gas storage vessels of this type comprise bulky structures and, apart from high capital costs, can hardly be installed, mainly from space considerations. The free space that exists between the surface of the biomass and the gas chamber cover can barely contain 5% of the daily gas production with the tower construction technology employed today.

In the future, BIOGAS plants can fulfill an appropriate purpose in the political economy as a substitute for fluid fossil fuels if there is success in mass production manufacture of these plants at favorable cost, with the simplest, most reliably operating construction and minimal mechanical expenditure.

The object of the present invention is to make agricultural operations with useful animal holdings or other operations that have anaerobically fermentable biomass at their disposal largely energy self-sufficient and independent of energy market forces.

The present invention therefore has for its purpose the provision of a plant for anaerobic fermentation of organic dry mass for the purpose of extracting a combustible gas with special regard to economic aspects. The most essential objectives that are sought are:

1. The fermentation chamber and the gas chamber of the plant should form one unit.
2. The fermentation chamber and the gas chamber should be equal in their volumes within the unit.
3. The fermentation chamber should be configured in an ideal hydraulic form.
4. The fermentation chamber should be able to take up and decompose a high concentration of organic dry material.
5. It must be possible for the biomass in the fermentation chamber to be mixed through substantially completely at intervals at the highest concentration of dry material.
6. The formation of a floating cover on the fluid surface in the fermentation chamber must be prevented.
7. It must be possible to hold the processing temperature of the biomass in the fermentation chamber at any desired temperature step between +10 and 36° C.
8. The plant should operate during charging operations as well as in continuous running.
9. The operating costs and the consumption of electrical energy should be low.
10. The plant should be fabricated of a material that is flexible and foldable, acid and gas proof and of high tensile strength.
11. It should be possible even for persons who are not experts to set up the plant.
12. The plant should be reliable and inexpensive to maintain, with the most simple construction, as well as having a long useful life.

The invention will be explained by way of example with reference to the figures, wherein.

Figure 1:
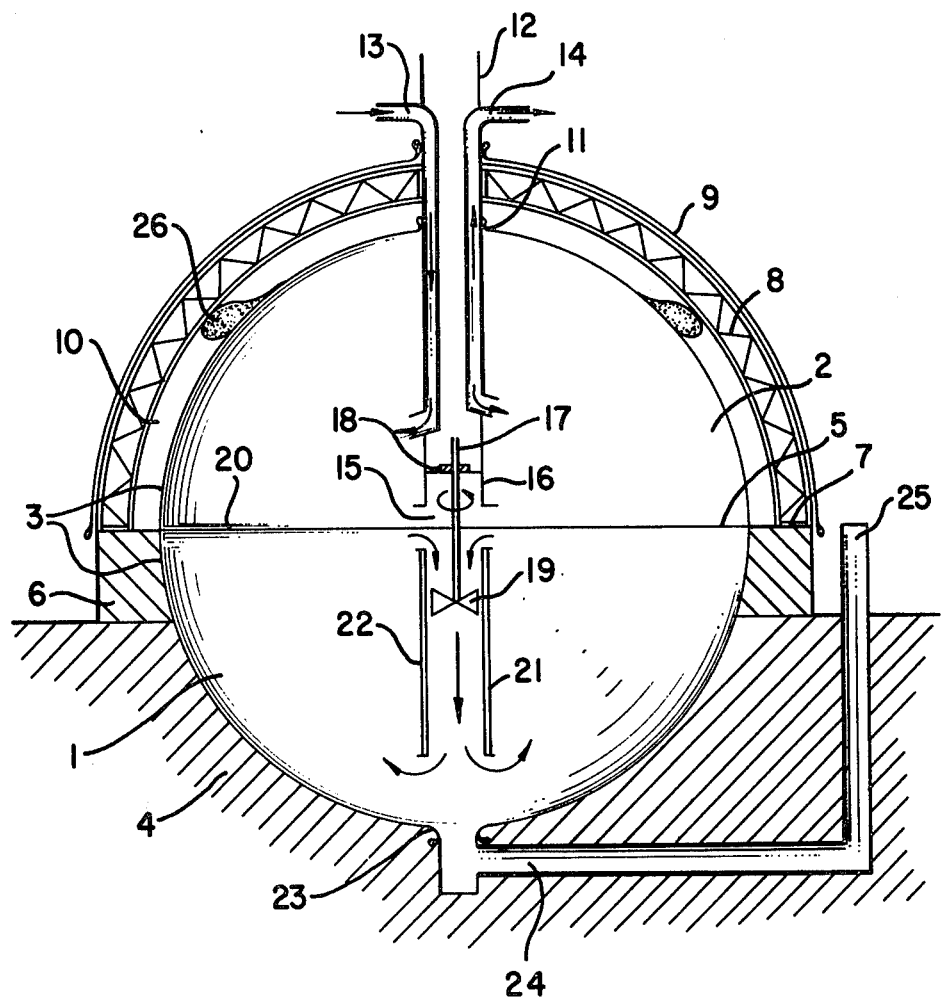
FIG. 1 is a vertical section through the tank that serves as the fermentation chamber and gas chamber, in the form of a geometrical hollow sphere with all process technology in place and built up, illustrated in the overpressure operating condition of the gas chamber.
Figure 2:
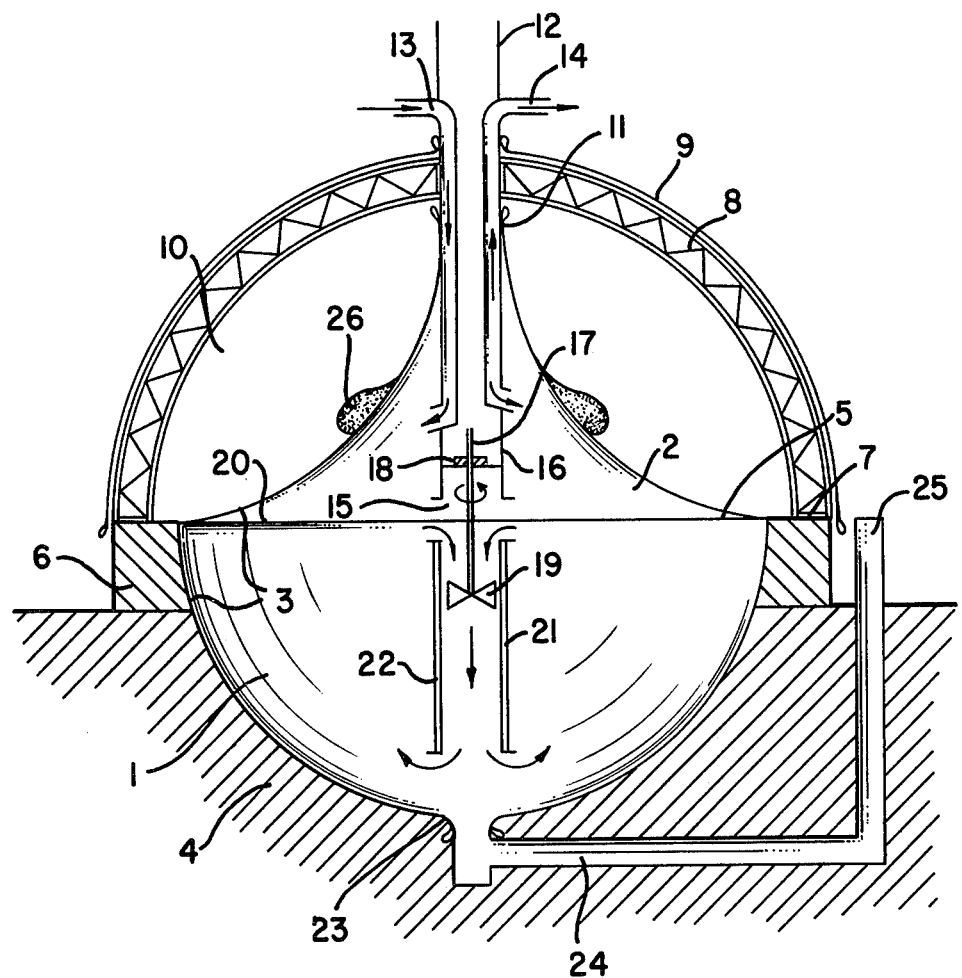
FIG. 2 is a vertical section through the tank that serves as the fermentation chamber and the gas chamber, in the form of a geometrical hollow sphere with all process technology in place and built up, illustrated in the unpressurized operating condition of the gas chamber.

An apparatus according to the invention, which makes possible the carrying out of the anaerobic fermentation process, is shown purely schematically in FIGS. 1 and 2.

The fermentation chamber 1 and the gas chamber 2 constitute a unit in the form of a geometrical hollow sphere 3 of flexible and foldable material, such as is illustrated for example by PVC film or rubberized woven textile.

The fermentation chamber 1 is embedded in a reinforced, pressure tight pit 4 in the form of a hemisphere, surrounded up to the level of the sphere equator by a form defining annular wall 6, preferably of cast-in-place or precast concrete parts.

The annular wall 6 at the same time serves as a foundation 7 for the supporting frame 8, which is preferably of prefabricated steel profiles, upon which is fastened the flexible and foldable cover 3 that forms a hemispherical gas chamber 2.

The supporting frame 8 at the same time serves as a carrier construction for a protective covering 9, which is separated from the gas chamber cover 3 by an annular air containing slot 10.

The covering of the gas chamber is apertured at its highest latitude, and through the aperture 11 a stack duct 12 passes into the interior of the hollow sphere 3, through the gas chamber 2 and into the fermentation chamber 1.

The stack duct 12 is held in a fixed position in the center of the hollow sphere by means of the supporting frame 8.

Built into the stack duct 12 is the charging duct 13, through which the fermentation chamber 1 is charged with material to be fermented, and the gas withdrawal duct 14, through which the gas collected in the gas chamber 2 is withdrawn.

On the line of the equator 5 of the sphere, the stack duct 12 has a number of openings 15. Above the openings 15, the stack duct 12 is sealed off from the gas chamber 2 by a gas tight partition 16. Through the gas tight partition 16, the drive shaft 17 leads by way of a stuffing box seal 18 to a screw pump 19 that is arranged beneath the openings 15 and is immersed in the material charge 20 in the fermentation chamber 1.

The portion of the stack duct 12 that is immersed in the material charge 20 in the fermentation chamber 1 is surrounded by a doubled sheathing 21, and hot water circulates in the annular groove 22 lying therebetween.

Below the lowest latitude, the covering 3 of the fermentation chamber 1 is apertured and the aperture 23 opens into a passage duct 24 that leads outside the hollow sphere and the outlet opening 25 of which lies at the level of the sphere equator.

The cover 3 of the gas chamber 2 is multiply weighted down at its exterior with weights 26 such as, for example, sand bags.

The apparatus in the form of a hollow sphere 3 that comprises the fermentation chamber 1 and the gas chamber 2 can for example have the following dimensions:

| | |
|---|---|
| Diameter: | 6.0 m (D) |
| Total volume: | 113.0 m³ (V) |
| Fermentation chamber volume: | 56.5 m³ (V) |
| Gas chamber volume: | 56.5 m³ (V) |

It can be operated as follows:

An essential prerequisite for the satisfactory functioning of such an apparatus for carrying out anaerobic fermentation for extraction of combustible gas is the preparation and the assembling of the biomass to be anaerobically fermented. This should contain the highest possible content of decomposable organic dry substance, and the total dry material should have a water content of not under 85% in order thus to be pumpable.

The biomass is delivered into the fermentation chamber portion of the spherical tank until the filling has reached the level of the equator of the sphere, whereupon excessive biomass is automatically displaced from the tank through the overflow passage that leads outside the tank. The outflow of the overflow passage lies on the same plane with the sphere equator and thereby serves as a filling limit for the fermentation chamber.

For optimal conduct of the anaerobic fermentation of the biomass, it must be warmed in the fermentation chamber to +36° C. This process temperature must be continuously maintained.

With the apparatus according to the present invention, the increase of the temperature level of the biomass to +36° C., as well as temperature maintenance, is obtained in that the portion of the stack duct that is centrally led into the fermentation chamber and is immersed in the biomass is formed as a heat exchanger.

By means of the large area openings in the stack duct wall, at the level of the surface of the biomass that also forms the equator of the sphere, the biomass is agitated from the top downwardly through the heat exchanger by means of a screw pump built into the heat exchanger portion of the stack duct, and the heat carried by the hot water that serves as a heating medium is thus transferred to the biomass.

Through the rotation of the screw pump, floating materials that rise up to the surface of the biomass are repeatedly sucked back down into the biomass through the stack duct.

By reversal of the direction of rotation of the screw pump, the biomass can also be moved from the bottom upwardly through the heat exchanger, which impedes the deposit of sedimentation on the fermentation chamber floor.

The combustible gas set free by the anaerobic fermentation of biomass, with a specific weight of 0.823 in comparison to air, collects under the folded together cover of the gas chamber, which is artificially weighted down by sandbags. With an increasing quantity of gas, there is a slow rise in the gas pressure, which is accurately defined by means of the weighting of the gas chamber cover, and it begins to inflate the folded together gas chamber cover to a hemisphere, until the working pressure predetermined by the weighting has been reached.

The working pressure within the gas chamber is maintained by means of a so-called water seal or water column, through which the excess gas, after the working pressure has been attained, can escape into the atmosphere.

If gas is withdrawn from the gas chamber by a consuming device, the weighted cover begins to fold together under the pressure balance obtained between the interior of the gas chamber and atmosphere and presses the gas out of the gas chamber under fluid pressure that remains constant.

If the gas requirement of the consuming device is satisfied the cover again begins to fill with gas.

If the fermentation chamber is charged with fresh, unfermented biomass at precisely defined time intervals, then at the same time fermented biomass is displaced out of the fermentation chamber through the overflow duct.

To impede heat loss, the total hollow spherical tank is surrounded by a heat insulation sheet and additionally the gas chamber is covered over with a weatherproof covering.

The here described process for carrying out anaerobic fermentation is essentially distinguished from other apparatus known today for carrying out this known process by the materials selected for it and its structural form.

The basic novelties relate both to the selection of a flexible and foldable material and to the selection of the geometrical form of a hollow sphere which serves at one and the same time as a fermentation tank and a gas reservoir.

Although flexible and foldable material has been employed for lining of basins or for providing containers, and gas accumulator vessels of this material in the form of hollow spheres or cylinders are also known in themselves, their combination in the apparatus according to the invention as well as the purpose to be achieved by them are basically new.

I claim:

1. Apparatus for anaerobic fermentation of organic slurry for the purpose of obtaining a combustible gas therefrom, characterized by:
    A. means defining a fermentation chamber having a top edge extending therearound that lies in a substantially horizontal plane and having a bottom surface which converges downwardly from said top edge to a central portion of said bottom surface;
    B. rigid supporting structure projecting above said plane;
    C. A cover of supple gas tight material extending across the fermentation chamber beneath said supporting structure to define a foldingly contractable and inflatably expandable gas chamber that is above said plane and in open communication with said fermentation chamber, said cover
        (1) having an edge portion that is sealed to said top edge of the fermentation chamber all around the same and
        (2) having a central portion which is fixedly supportingly connected to said supporting structure at a level substantially above said plane;
    D. weighting means attached to said cover at locations spaced from said central portion thereof and from said edge portion thereof, for gravity loading the cover so that it tends to contract and maintain gas in said gas chamber under pressure;
    E. an upright stack duct supported near an upper end thereof by said supporting structure and extending downwardly through said central portion of the cover, in sealed relation thereto, to near said central portion of the bottom surface, said stack duct
        (1) having apertures therein at substantially the level of said plane and
        (2) comprising means for charging slurry into said fermentation chamber and for withdrawing gas from said gas chamber;
    F. a screw pump in said stack duct, below said apertures therein, for pumping slurry between said apertures and the bottom end of the stack duct and thereby agitating slurry in the fermentation chamber; and
    G. means cooperating with the portion of said stack duct that is below said plane to provide a fluid chamber through which heated fluid is circulated for heating the contents of said fermentation chamber.

2. The apparatus of claim 1, further characterized by:
    H. an overflow duct having an inlet in said central portion of the bottom surface and having an outlet external to the fermentation chamber, at the level of said plane, for preventing slurry in the fermentation chamber from rising above the level of said plane.

3. The apparatus of claim 1 wherein said means cooperating with the portion of the stack duct that is below said plane comprises a wall concentric to that portion of the stack duct and which cooperates therewith to define an annular fluid chamber.

4. The apparatus of claim 1, further characterized by: said screw pump being reversible for alternatively and selectably drawing sediment up from the central portion of the fermentation chamber and dispersing it through said apertures or drawing floating materials off of the surface of slurry in the fermentation chamber through said apertures and forcing it down towards said central portion of the bottom surface.

5. The apparatus of claim 1, wherein said rigid supporting structure comprises a framework that substantially defines a hemisphere, and said central portion of the cover and said stack duct are connected to the uppermost portion of said framework, further characterized by:
    a covering over the exterior of said framework to thermally insulate said gas chamber from the ambient atmosphere.

* * * * *